(12) United States Patent
Liu (10) Patent No.: US 11,648,215 B2
(45) Date of Patent: May 16, 2023

(54) MICROCELL SYSTEMS FOR DELIVERING HYDROPHILIC ACTIVE MOLECULES

(71) Applicant: E Ink California, LLC, Fremont, CA (US)

(72) Inventor: Lei Liu, Fremont, CA (US)

(73) Assignee: E INK CALIFORNIA, LLC, Fremont, CA (US)

( * ) Notice: Subject to any disclaimer, the term of this patent is extended or adjusted under 35 U.S.C. 154(b) by 37 days.

(21) Appl. No.: 17/505,899

(22) Filed: Oct. 20, 2021

(65) Prior Publication Data

US 2022/0133645 A1 May 5, 2022

Related U.S. Application Data

(60) Provisional application No. 63/107,150, filed on Oct. 29, 2020.

(51) Int. Cl.
*A61K 9/70* (2006.01)
*A61K 47/32* (2006.01)
*A61K 47/34* (2017.01)

(52) U.S. Cl.
CPC ............ *A61K 9/7092* (2013.01); *A61K 47/32* (2013.01); *A61K 47/34* (2013.01)

(58) Field of Classification Search
None
See application file for complete search history.

(56) References Cited

U.S. PATENT DOCUMENTS

| 4,559,222 A | 12/1985 | Enscore et al. |
| 4,640,689 A | 2/1987 | Sibalis |
| 4,666,441 A | 5/1987 | Andriola et al. |
| 4,734,090 A | 3/1988 | Sibalis |
| 5,125,894 A | 6/1992 | Phipps et al. |
| 5,135,479 A | 8/1992 | Sibalis et al. |
| 5,486,362 A | 1/1996 | Kitchell et al. |
| 5,533,995 A | 7/1996 | Corish et al. |
| 5,591,767 A | 1/1997 | Mohr et al. |
| 5,603,693 A | 2/1997 | Frenkel et al. |
| 5,658,592 A | 8/1997 | Tanihara et al. |
| 5,736,154 A | 4/1998 | Fuisz |
| 5,797,898 A | 8/1998 | Santini, Jr. et al. |

(Continued)

FOREIGN PATENT DOCUMENTS

| EP | 1457233 A1 | 9/2004 |
| JP | 2015151380 A | 8/2015 |

(Continued)

OTHER PUBLICATIONS

Korean Intellectual Property Office, "International Search Report & Written Opinion", PCT/US2021/055141, dated Jan. 28, 2022. Jan. 28, 2022.

(Continued)

*Primary Examiner* — Brian Gulledge
(74) *Attorney, Agent, or Firm* — Ioannis Constantinides (57) ABSTRACT

A hydrophilic active molecule delivery system whereby active molecules can be released on demand and/or a variety of different active molecules can be delivered from the same system and/or different concentrations of active molecules can be delivered from the same system. The system may be used to deliver/release hydrophilic active molecules that are incompatible to each other.

19 Claims, 9 Drawing Sheets

(56) References Cited

U.S. PATENT DOCUMENTS

| | | |
|---|---|---|
| 5,931,804 A | 8/1999 | Sibalis |
| 5,980,943 A | 11/1999 | Ayer et al. |
| 6,123,861 A | 9/2000 | Santini, Jr. et al. |
| 6,521,191 B1 | 2/2003 | Schenk et al. |
| 6,564,093 B1 | 5/2003 | Ostrow et al. |
| 6,565,532 B1 | 5/2003 | Yuzhakov et al. |
| 6,757,560 B1 | 6/2004 | Fischer et al. |
| 6,791,003 B1 | 9/2004 | Choi et al. |
| 6,933,098 B2 | 8/2005 | Chan-Park et al. |
| 6,980,855 B2 | 12/2005 | Cho |
| 7,229,556 B1 | 6/2007 | Hinds, III et al. |
| 7,279,064 B2 | 10/2007 | Daniel et al. |
| 7,315,758 B2 | 1/2008 | Kwiatkowski et al. |
| 7,383,083 B2 | 6/2008 | Fischer et al. |
| 7,392,080 B2 | 6/2008 | Eppstein et al. |
| 7,537,590 B2 | 5/2009 | Santini, Jr. et al. |
| 7,604,628 B2 | 10/2009 | Santini, Jr. et al. |
| 7,611,481 B2 | 11/2009 | Cleary et al. |
| 7,715,088 B2 | 5/2010 | Liang et al. |
| 7,892,221 B2 | 2/2011 | Santini, Jr. et al. |
| 8,095,213 B1 | 1/2012 | Sexton |
| 8,257,324 B2 | 9/2012 | Prausnitz et al. |
| 8,403,915 B2 | 3/2013 | Santini, Jr. et al. |
| 8,440,222 B2 | 5/2013 | Hausner et al. |
| 8,517,958 B2 | 8/2013 | Eppstein et al. |
| 8,696,637 B2 | 4/2014 | Ross |
| 8,744,569 B2 | 6/2014 | Imran |
| 8,830,561 B2 | 9/2014 | Zang et al. |
| 8,862,223 B2 | 10/2014 | Yanaki |
| 8,962,014 B2 | 2/2015 | Prinz et al. |
| 8,968,699 B2 | 3/2015 | Jin et al. |
| 9,186,317 B2 | 11/2015 | Smyth et al. |
| 9,188,829 B2 | 11/2015 | Li et al. |
| 9,320,720 B2 | 4/2016 | Maier |
| 9,326,979 B2 | 5/2016 | Kimura et al. |
| 9,327,105 B2 | 5/2016 | Ramdas et al. |
| 9,388,307 B2 | 7/2016 | Li et al. |
| 9,610,440 B2 | 4/2017 | Jordan et al. |
| 9,931,296 B2 | 4/2018 | Doshi |
| 9,968,549 B2 | 5/2018 | Kosel et al. |
| 10,087,344 B2 | 10/2018 | Moran |
| 10,918,846 B2 | 2/2021 | Nagai et al. |
| 10,933,029 B2 | 3/2021 | Liu |
| 2005/0191337 A1 | 9/2005 | Gueret |
| 2006/0009731 A1 | 1/2006 | Wu et al. |
| 2006/0257450 A1 | 11/2006 | Mudumba et al. |
| 2006/0269475 A1 | 11/2006 | Ryu et al. |
| 2007/0196456 A1 | 8/2007 | Stevens et al. |
| 2007/0248657 A1 | 10/2007 | Smith et al. |
| 2007/0292463 A1 | 12/2007 | Spector |
| 2008/0020007 A1 | 1/2008 | Zang |
| 2009/0234214 A1 | 9/2009 | Santini, Jr. et al. |
| 2010/0143448 A1 | 6/2010 | Nisato et al. |
| 2010/0189793 A1 | 7/2010 | Meyer et al. |
| 2011/0046557 A1 | 2/2011 | Lee et al. |
| 2011/0111013 A1 | 5/2011 | Salman et al. |
| 2011/0196474 A1 | 8/2011 | Davalian et al. |
| 2013/0096486 A1 | 4/2013 | Schroeder et al. |
| 2014/0330223 A1 | 11/2014 | Schurad et al. |
| 2015/0301425 A1 | 10/2015 | Du et al. |
| 2016/0045158 A1 | 2/2016 | Hsu |
| 2016/0279072 A1 | 9/2016 | Li et al. |
| 2017/0205649 A1 | 7/2017 | Wang et al. |
| 2018/0271800 A1 | 9/2018 | Liu et al. |
| 2019/0142763 A1* | 5/2019 | Liu ..................... A61K 9/7084 424/449 |
| 2020/0138733 A1 | 5/2020 | Liu |

FOREIGN PATENT DOCUMENTS

| | | |
|---|---|---|
| KR | 19980025307 A | 7/1998 |
| WO | 2009073686 A1 | 6/2009 |

OTHER PUBLICATIONS

Korean Intellectual Property Office, "International Search Report & Written Opinion," PCT/US2021/054976, dated Jan. 28, 2022. Jan. 28, 2022.

Thomas.G. Harvey., "Replication techniques for micro-optics"., Proc. vol. 3099, pp. 76-82 (1997) Sep. 24, 1997.

Harvey, T.G.; "Replication techniques for micro-optics"; SPIE Proc. vol. 3099, pp. 76-82; 1997. Jan. 1, 1997.

Ebbert Jon O. et al., "Combination Pharmacotherapy for Stopping Smoking: What Advantages Does it Offer?", Drugs, vol. 70 No. 6, pp. 643-650, (Apr. 16, 2010). Apr. 16, 2010.

Kaiyong Cai et al., "Magnetically triggered reversible Controlled Drug Delivery from Microfabricated Polymeric Multireservior Devices"., Advanced Materials. 2009, 21, 4045-4049 May 28, 2009.

Korean Intellectual Property Office, PCT/US2018/023917, International Search Report and Written Opinion, dated Jul. 10, 2017. Jul. 10, 2018.

Korean Intellectual Property Office, PCT/US2018/023928, International Search Report and Written Opinion, dated Jul. 10, 2018. Jul. 10, 2018.

Korean Intellectual Property Office, PCT/US2018/023921, International Search Report and Written Opinion, dated Jul. 10, 2018. Jul. 10, 2018.

Korean Intellectual Property Office, PCT/US2018/060259, International Search Report and Written Opinion, dated Apr. 29, 2019. Apr. 29, 2019.

Korean Intellectual Property Office, PCT/US2018/060266, International Search Report and Written Opinion, dated Apr. 29, 2019. Apr. 29, 2019.

Xuan, Shouhu et al., "Systhesis of Fe3O4@Polyaniline Core/Shell Microspheres with Well-Defined Blackberrym-Like Morphology", J. Phys. Chem. C., vol. 112, pp. 18804-18809. (2008). Oct. 3, 2008.

Sahoo et al., "A Review of Transdermal drug delivery system", Journal der Pharmazie Forschung, vol. 2, N-1, 2013, 32-56 (2013) 2013.

Huang, W. C. et al.., "A flexible drug delivery chip for the magnetically-controlled release of anti-epileptic drugs", Journal of Controlled Release, vol. 139, Issue 3, Nov. 3, 2009, pp. 221-228 Nov. 3, 2009.

European Patent Office, EP Appl. No. 18771343.3, Extended European Search Report, dated Aug. 14, 2020. Aug. 14, 2020.

Gulati Gaurav Kumar et al., "Programmable carbon nanotube membrane-based transdermal nicotine delivery with microdialysis validation assay", Nanomedicine: Nanotechnology, Biology and medicine, Elsevier, NL, vol. 13, No. 1, Jul. 18, 2016, p. 1-9, XP029879755, ISSN: 1549-9634 (Jul. 18, 2016) Jul. 18, 2016.

Im J S et al., "The effect of carbon nanotubes on drug delivery in an electro-sensitive transdermal drug delivery system" Biomaterials, Elsevier, Amsterdam, NL, vol. 31, No. 6, Feb. 1, 2010, pp. 1414-1419, XP026814171, ISSN: 0142-9612 ( Feb. 1, 2020) Feb. 1, 2010.

European Patent Office, EP. Appl. No. 18772394.5, European Search Report, dated Nov. 30, 2020. Nov. 30, 2020.

European Patent Office, EP. Appl. No. 18771792.1, Supplemental Partial European Search Report, dated Nov. 24, 2020. Nov. 24, 2020.

European Patent Office, EP. Appl. No. 18771792.1, Extended European Search Report, dated Mar. 31, 2021 Mar. 31, 2021.

* cited by examiner

First type of microcells

Second type of microcells

Third type of microcells

First type of microcells

Third type of microcells

MICROCELL SYSTEMS FOR DELIVERING HYDROPHILIC ACTIVE MOLECULES

RELATED APPLICATIONS

This application claims priority to U.S. Provisional Patent Application No. 63/107,150, filed on Oct. 29, 2020. The entire contents of any patent, published application, or other published work referenced herein is incorporated by reference.

BACKGROUND

Hydrophilic active molecules, such as vitamins, antibiotics (e.g., penicillin), and salts of certain compounds, are often stabilized in a matrix or gel for delivery with a transdermal system. Matrices and gels require a large quantity of non-active materials (e.g., cellulose, cyclodextrin, polyethylene oxide), and the amount of hydrophilic active molecules that can be captured into, and released from, the matrix may be limited. Additionally, the active molecules may crystalize within the matrix during storage, limiting the shelf life of the delivery system. Because of these limitations, the amount of hydrophilic active molecule that can be delivered with a "standard" amount of matrix or gel may not be sufficient for all patients. Consequently, if a "high" dose is required, a physician will direct a patient to place multiple matrix-containing transdermal patches, or direct the patient to apply the gel several times during the day. A system that allows more variability in the concentrations of these active molecules, as well as more precise control of the release profile, is desirable. Furthermore, in the case of delivery of combination of active molecules, it is possible that the different active molecules are not compatible with each other and one or both of them may degrade if they are in the presence of the other for more than a certain time period. A system than can deliver such incompatible active molecules is desirable.

SUMMARY

The invention addresses these needs by providing an active molecule delivery system whereby hydrophilic active molecules can be prepared in simple aqueous formulations and then delivered at the desired location. Furthermore, the systems of the invention allow for the delivery of different types, and/or concentrations, and/or volumes of hydrophilic active molecules from the same delivery system.

In one aspect the invention is an active molecule delivery system including a layer of microcells, the layer of microcells comprising: a plurality of a first type of microcells filled with a first aqueous formulation comprising a first hydrophilic active molecule; a plurality of a second type of microcells filled with a second aqueous formulation comprising a second hydrophilic active molecule, wherein the first and second active molecules are different; a plurality of a third type of microcells that do not contain any formulation that comprise a hydrophilic active molecule. The plurality of the third type of microcells may contain no aqueous formulation. In one embodiment, each microcell of the first, second, and third types of microcells includes walls and an opening. The microcells may be square, round, or polygonal, such as a honeycomb structure. Each microcell of the first and second types of microcells includes a hydrophobic sealing layer spanning the opening. At least one microcell of the first type of microcells does not have any adjacent microcell of the second type of microcells in the layer of microcells. The hydrophobic sealing layer may be constructed from a variety of materials, such as polyisobutylene, a polyethylene, a polyurethane, a polycaprolactone, or a polysiloxane. In some embodiments, the hydrophobic sealing layer is spanned by a porous diffusion layer. The porous diffusion layer may be constructed from a variety of materials, such as acrylate, methacrylate, polycarbonate, polyvinyl alcohol, cellulose, poly(N-isopropylacrylamide) (PNIPAAm), poly(lactic-co-glycolic acid) (PLGA), polyvinylidene chloride, acrylonitrile, amorphous nylon, oriented polyester, terephthalate, polyvinyl chloride, polyethylene, polypropylene, polybutylene, polyisobutylene, or polystyrene. Typically, each microcell has a volume greater than 100 nL. In some embodiments, the porous diffusion layer has an average pore size of between 0.1 nm and 100 nm. The hydrophilic active molecule can be any active molecule that is soluble or partially soluble in water, including pharmaceutical compounds, aroma compounds (e.g., perfumes), nucleic acids (e.g., DNA, RNA), or amino acids (e.g., proteins, e.g., vaccines, antibodies, or enzymes). The active molecule delivery system may comprise microcells of the first type of microcells that are filled with a first aqueous formulation of a first concentration of the first hydrophilic active molecule and other microcells of the first type of microcells that are filled with a first aqueous formulation of a second concentration of the first hydrophilic active molecule, wherein the first and second concentrations are different. In another embodiment, the system may comprise microcells of the first type of microcells that includes first volume of a first aqueous formulation of the first hydrophilic active molecule and other microcells of the first type of microcells that include a second volume of the first aqueous formulation of the first hydrophilic active molecule, wherein the first and the second volumes are different.

In one embodiment, each of the first type microcells does not have any adjacent second type of microcells in the layer of microcells. In another embodiment, the plurality of the third type of microcells does not include a sealing layer spanning the opening. Each of the first and second types of microcells may further comprise an adhesive layer adjacent to the hydrophilic sealing layer. The adhesive layer may be biocompatible. In another embodiment, the plurality of first type of microcells further comprises a first porous diffusion layer between the hydrophobic sealing layer and the adhesive layer, and the plurality of second type of microcells further comprises a second porous diffusion layer between the hydrophobic sealing layer and the adhesive layer. The first porous diffusion layer may have average pore size that is larger than the average pore size of the second porous diffusion layer.

In another aspect, the invention is an active molecule delivery system including a layer of microcells, the layer of microcells comprising: a plurality of a first type of microcells filled with a first aqueous formulation comprising a first hydrophilic active molecule; a plurality of a third type of microcells filled with a third aqueous formulation that does not contain any active molecules. Each microcell of the first and third types includes walls and an opening and each microcell of the first and third types includes a hydrophobic sealing layer spanning the opening. The active molecule delivery system comprises one or more segments of the first type of microcells, wherein each segment of the first type of microcells exclusively comprises only microcells of the first type of microcells, and wherein all the microcells of the first type of microcells that are adjacent to any other microcell of the segment of the first type of microcells are members of the same segment, and wherein the periphery of at least one segment of the first type of microcells is surrounded by microcells of the third type of microcells. The active molecule delivery system may further comprise a plurality of a second type of microcells filled with a second aqueous formulation comprising a second hydrophilic active molecule, wherein the first and second hydrophilic active molecules are different. Each microcell of the second type of microcells includes walls and an opening. Each microcell of the second type includes a hydrophobic sealing layer spanning the opening. The active molecule delivery system may comprise one or more segments of the second type of microcells, wherein each segment of the second type of microcells exclusively comprises only microcells of the second type of microcells, and all the microcells of the second type of microcells that are adjacent to any other microcell of the segment of the second type of microcells are members of the same segment, and wherein the periphery of at least one segment of the second type of microcells is surrounded by microcells of the third type of microcells. Each of the first type microcells does not have any adjacent second type of microcells in the layer of microcells. The plurality of the first, second and third type of microcells may further comprise a porous diffusion layer adjacent the hydrophobic sealing layer. In some embodiments, the first and second aqueous formulations will include additional components such as thickening agents, colorants, adjuvants, vitamins, salts, or buffering agents. The aqueous formulations may also include charge control agents, surfactants, and preservatives.

The active molecule delivery system may be used for transdermal delivery of an active molecule or for delivery of an active molecule in any other location.

BRIEF DESCRIPTION OF THE DRAWINGS

FIG. 2C illustrates an example of an active molecule delivery system including a plurality of a first type of microcells and a plurality of a second type of microcells separated by a plurality of a third type of microcells; the first and second types of microcells comprise a hydrophobic sealing layer and a porous diffusion layer. In the example of FIG. 2C, the first type of microcells and the second type of microcells include different porosities in the porous diffusion layer and thus have different delivery profiles. The different delivery profiles may be achieved by (a) having different average pore diameters and/or (b) different porous diffusion layer thicknesses in different types of microcells. Furthermore, a different polymer may be used for making the porous diffusion layer of the different types of microcells.

FIGS. 5C and 5D detail an alternate embodiment in which microcells for an active molecule delivery system are fabricated using photolithography. In FIGS. 5C and 5D a combination of top and bottom exposure is used, allowing the walls in one lateral direction to be cured by top photomask exposure, and the walls in another lateral direction to be cured bottom exposure through the opaque base conductor film.

DESCRIPTION

The invention provides a hydrophilic active molecule delivery system whereby active molecules can be released on demand and/or a variety of different active molecules can be delivered from the same system and/or different concentrations of active molecules can be delivered from the same system. The invention is well suited for delivering hydrophilic pharmaceuticals to patients transdermally. However, the invention may be used to deliver hydrophilic active molecules on surfaces or in spaces, generally. For example, the invention can be used to deliver larger molecules that need to be kept in an aqueous buffered environment, such as enzymes or antibodies. The active molecule delivery system includes a plurality of microcells, wherein the microcells are filled with a medium including the hydrophilic active molecules. The microcells include an opening, which is spanned by a hydrophobic sealing layer. The sealing layer may be overcoated with a porous diffusion layer.

In addition to more conventional applications, such as transdermal delivery of pharmaceutical compounds, the active molecule delivery system may be the basis for delivering agricultural nutrients. For example, the microcell arrays can be fabricated into large sheets that can be used in conjunction with hydroponic growing systems, or the microcell arrays can be integrated into hydrogel film farming. See, for example, Mebiol, Inc. (Kanagawa, Japan). The active molecule delivery systems can also be incorporated into the structural walls of smart packing. Such delivery systems makes it possible to have long term release of antioxidants into a package containing fresh vegetables. This "smart"

packaging will dramatically improve the shelf life of certain foods, and it will only require the amount of antioxidant necessary to maintain freshness until the package is opened. Thus, the same packaging can be used for food that is distributed locally, across the country, or around the globe. The active molecule delivery system may also delivery active molecules in many other uses via a film, such as on aromatic materials (air care), anti-microbial compounds on surfaces, etc.

The term "active molecule" includes a pharmaceutical, cosmetic, aromatic, anti-microbial, anti-oxidant, and other benefit agents. It also includes molecules that enhance or activate the benefit of the benefit agent.

The term "segment of the first type of microcells" means a set of microcells that comprises exclusively microcells the first type of microcells; and all the microcells of the first type of microcells that are adjacent to any other microcell of the segment of the first type of microcells are members of the same segment. Analogously, the terms "segment of the second type of microcells", "segment of the third type of microcells" and so on, are defined. That is, a segment is a set of microcells of the A type of microcells that occupy an area, wherein all of the microcells in the area are of the same (A) type of microcells and there are no microcells that are adjacent to any of the microcell of the segment that are of the A type that are not part of the segment.

The term "adjacent microcells" refers to microcells of the active molecule delivery system that share a wall. That is, adjacent microcells are microcells that are next to each other.

The term "porous diffusion layer" includes any film that has average pores from 0.1 nm to 100 μm.

The term "filled" in relation to a microcell (or microcells) mean that a formulation is present in the microcell (or microcells). It does not necessarily mean that the whole volume of the microcell is occupied by the formulation. In other words, the term "filled" in reference to a microcell (or microcells) include the concepts of a partially filled microcell (or microcells) as well as a completely "filled" microcell (or microcells). Analogously, filling a microcell (or microcells) means that a formulation is added into a microcell (or microcells). It does not necessarily mean that sufficient amount of the formulation is being added into the microcell to occupy its entire volume.

The invention also provides a system for simple and low cost delivery of combinations of active molecules over a period of time. Such a delivery system may be used, for example, as an emergency delivery system for a person undergoing an allergic reaction. The system may include epinephrine, as well as antihistamines. The device can be applied and then triggered to cause the active molecules to be quickly passed through the skin. The system may be particularly effective as a back-up system for small children who may be exposed to life-threatening allergens while on a field trip, etc. A parent can affix the delivery system to the child with instructions to activate the device in the event of, e.g., a bee sting. Because the device is relatively simple, compliance with proper delivery protocols will be greater than, e.g., an epipen.

In one embodiment, the active molecule delivery system comprises a first, second, and third types of microcells, wherein the plurality of a first type of microcells filled with a first aqueous formulation comprising a first hydrophilic active molecule, the plurality of a second type of microcells filled with a second aqueous formulation comprising a second hydrophilic active molecule, a plurality of a third type of microcells that do not contain any formulation comprising an active molecule, and wherein each of the first type microcells does not have any adjacent second type of microcells in the layer of microcells.

Figure 1:
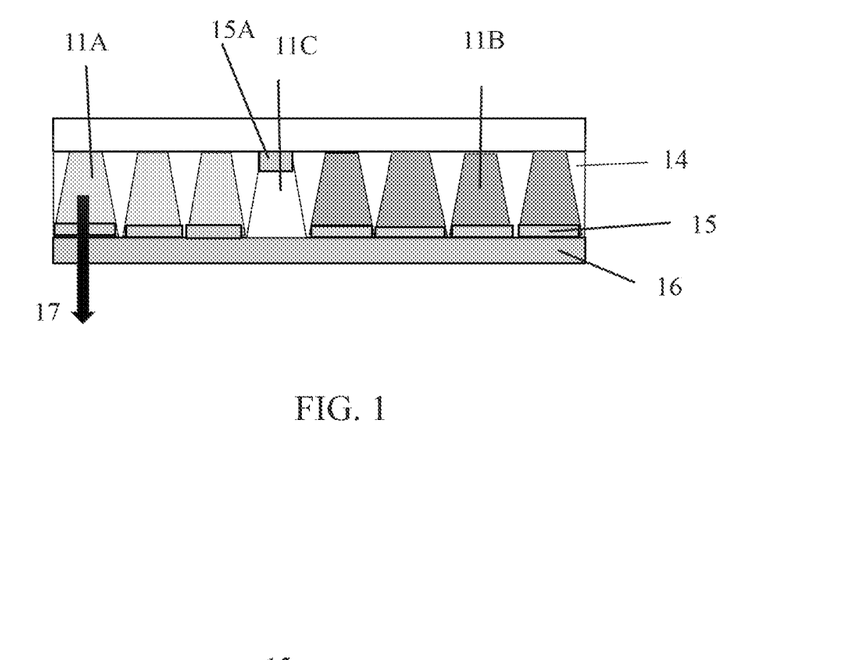
FIG. 1 illustrates an example of a hydrophilic active molecule delivery system including a plurality of first, second, and third type of microcells. The first and second types of microcells contain aqueous formulations including hydrophilic active molecules. The microcells of the first and second types of microcells are sealed with a hydrophobic sealing layer, and the system additionally includes an adhesive layer.

An overview of a hydrophilic active molecule delivery system is shown in FIG. 1. The system includes a plurality of a first type of microcells 11A, a plurality of a second type of microcells 11B, and a plurality of a third type of microcells 11C. Each microcell of the first and second types includes an aqueous medium (also called. internal phase), that includes hydrophilic active molecules. Each microcell of the first and second types includes a wall 14 and an opening, which is sealed with a hydrophobic sealing layer 15. The hydrophobic sealing layer may be constructed from, e.g., polyisobutylene, a polyethylene, a polyurethane, a polycaprolactone, or a polysiloxane. The delivery system additionally includes an adhesive layer 16, which may include, for example, a polyisobutylene, an acrylic, a poly(ethylene)glycol, or a silicone. The microcells of the first type 11A and the microcells of the second type 11B are separated by a microcell of a third type 11C, which does not contain any active molecule formulation. As shown in FIG. 1, the opening of the microcell of the third type 11C do not comprise a sealing layer. The material of the sealing composition has been deposited on the side of the microcell that is opposite to the opening of the microcell 11C. In the case of the first and second types of microcells, the sealing composition is applied on microcells that are filled with aqueous formulation comprising hydrophilic active molecules. Thus, the sealing composition is formed on the opening of each individual microcells as shown in FIG. 1 (or above it as a common sealing film). In the case of the empty microcells of the third type of microcells, the applied sealing composition is deposited on side of the microcell opposite to the opening side. The active molecules of microcells 11A and 11B are delivered from the active molecule delivery system through sealing layer 15 and adhesive layer 16. The release direction 17 of the active molecules is shown in FIG. 1 by the arrow.

Figure 2A:
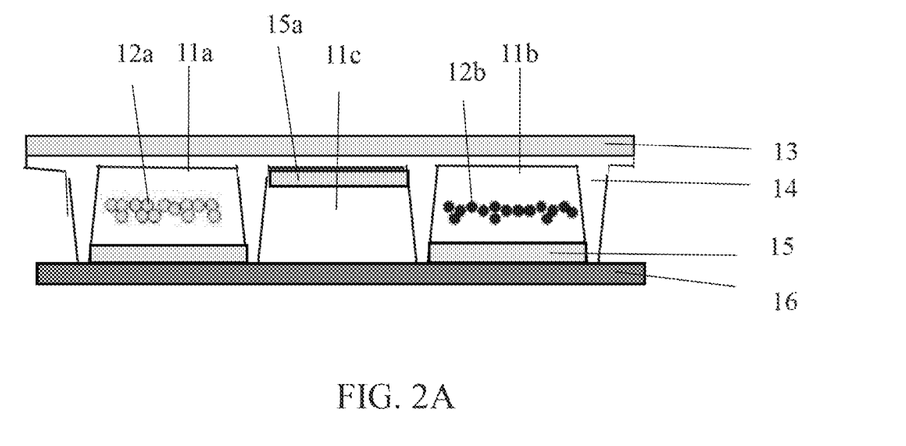
FIG. 2A illustrates an example of an active molecule delivery system including first, second, and third types of microcells. The first and second types of microcells include a hydrophobic sealing layer. The first type of microcells comprise a first active molecule and the second type of microcells comprise a second active molecule.

As shown in FIG. 2A, a first microcell 11a may include a first aqueous formulation 12a comprising a first hydrophilic active molecule, while a second microcell 11b includes a second aqueous formulation 12b comprising a second hydrophilic active molecule, while a third microcell 11c is located in-between microcell 11a and 11b and it does not include any active molecule formulation. Each microcell is part of an array that is formed from a polymer matrix, which is described in more detail below. The active molecule delivery system will typically include a backing barrier 13 to provide structural support and protection against ingress of molecules and physical interactions. The microcells are defined by walls 14 that are at least 1 μm high, although they can be much higher depending upon the desired depth of the microcell. The microcells may be arranged as squares, a honeycomb, circles, etc. Microcells 11a and 11b comprise a porous sealing layer 15. Often microcells additionally include an adhesive layer 16 that is also porous to the active molecule. The adhesive layer 16 assists in keeping the active molecule delivery system adjacent to a surface. As explained above, the sealing composition of the microcell of the third type 11c is deposited at the surface opposite to the side of the opening.

Figure 2B:
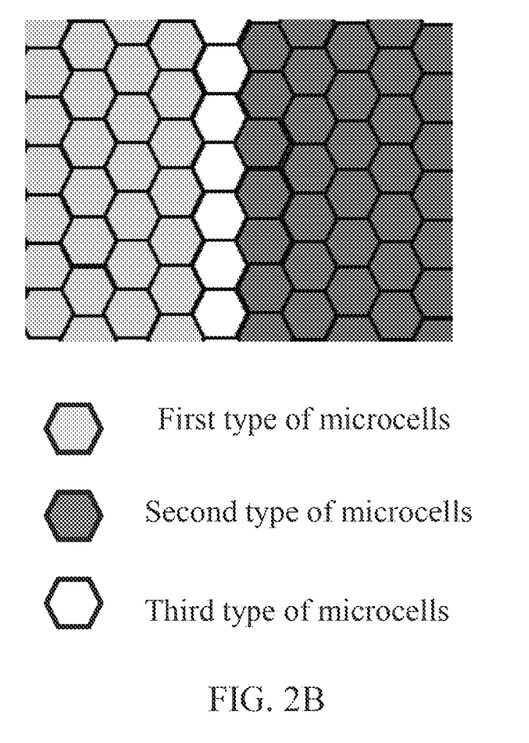
FIG. 2B illustrates an example of an active molecule delivery system having a first, second, and third types of microcells viewed from the top.

FIG. 2B illustrates a similar system of microcells as of FIG. 2A viewed from above. A plurality of the first type microcells are separated from a plurality of the second type of microcells by a plurality of the third type of microcells, which do not contain any active molecule formulation.

The delivery system may also include a porous diffusion layer, which may be constructed from a variety of natural or non-natural polymers, such as acrylates, methacrylates, polycarbonates, polyvinyl alcohols, cellulose, poly(N-isopropylacrylamide) (PNIPAAm), poly(lactic-co-glycolic acid)(PLGA), polyvinylidene chloride, acrylonitrile, amorphous nylon, oriented polyester, terephthalate, polyvinyl chloride, polyethylene, polypropylene, polybutylene, polyisobutylene, or polystyrene. Using picoliter injection with inkjet or other fluidic systems, individual microcells can be filled to enable a variety of different active molecules to be included in an active molecule delivery system.

Figure 2C:
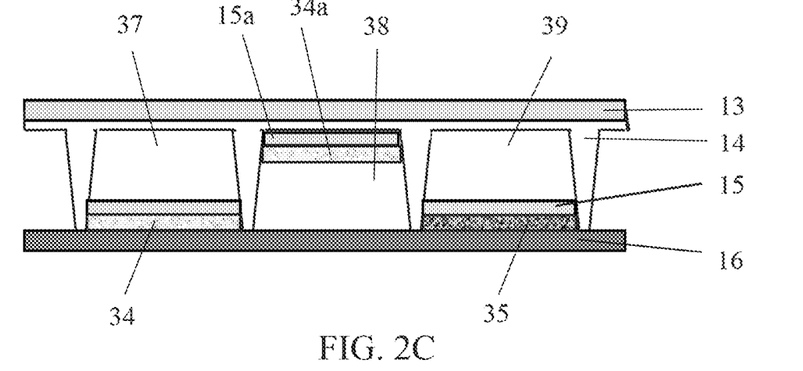

FIG. 2C shows another embodiment of a hydrophilic active molecule delivery system in which the porosity of the diffusion layer is varied for different microcells. This can be accomplished by using different polymer materials and microinjection, e.g., using inkjet during the sealing process (described below). Such systems allow a single delivery system to administer varying concentrations of the same or different active molecules over a period of time. For example, a system of the invention may include three microcells 37, 38, 39. Microcell 38 does not contain any active molecule formulation, whereas microcells 37 and 39 comprise folic acid at two different concentrations. However, the dosage time will be controlled by the porosity of the diffusion layer. For example, shortly after application the most concentrated dose may be delivered via microcell 37 via the most porous diffusion layer 34, followed by a less concentrated dose delivered from microcell 39 via the second diffusion layer 35. As described above, the sealing composition and the composition that forms the porous diffusion layer 34a are deposited on the opposite side of the opening side in the microcell 34a, which is a microcell of the third type of microcell. FIG. 2C shows example of an active molecule delivery system wherein the sealing layers 15 of the first and second types of microcells 37 and 39 are located below the surface of the opening of the microcells, that is, inside the microcells. The porous diffusion layers 34 and 35, which are adjacent to the sealing layers, may also be located below the surface of the opening of the microcells, that is, inside the microcells. However, in a different active molecule delivery system of the present invention, the sealing layers and the porous diffusion layers may be above the surface of the opening of the microcells, that is, outside of the microcells, as common films. In another example, the active molecule delivery system may comprise microcells of the first and second types, wherein the sealing layers are inside the microcells and the porous diffusion layers are outside the microcells. Furthermore, the adhesive layer 16 is optionally present.

The first type of microcells may be present in the system as one segment of the first type of microcells. The second type of microcells may also be present in the system as one segment of the second type of microcells. The segment of the first type of microcells may be separated from the segment of the second type of microcell by a segment of the third type of microcells. In other embodiments of the present invention, the first type of microcells occur in the system as two, three or more segments, and the second type of microcells also occur in the system as two, three or more segments, and each of the first type of microcells does not have any adjacent microcell of the second type of microcells. Each of the first type of microcells may be separated by any microcell of the second type of microcells by at least one microcell of the third type of microcells. Alternatively, each of the first type of microcells may be separated by any microcell of the second type of microcells by at least two, three, four, five, or more microcells of the third type of microcells.

Figure 3:
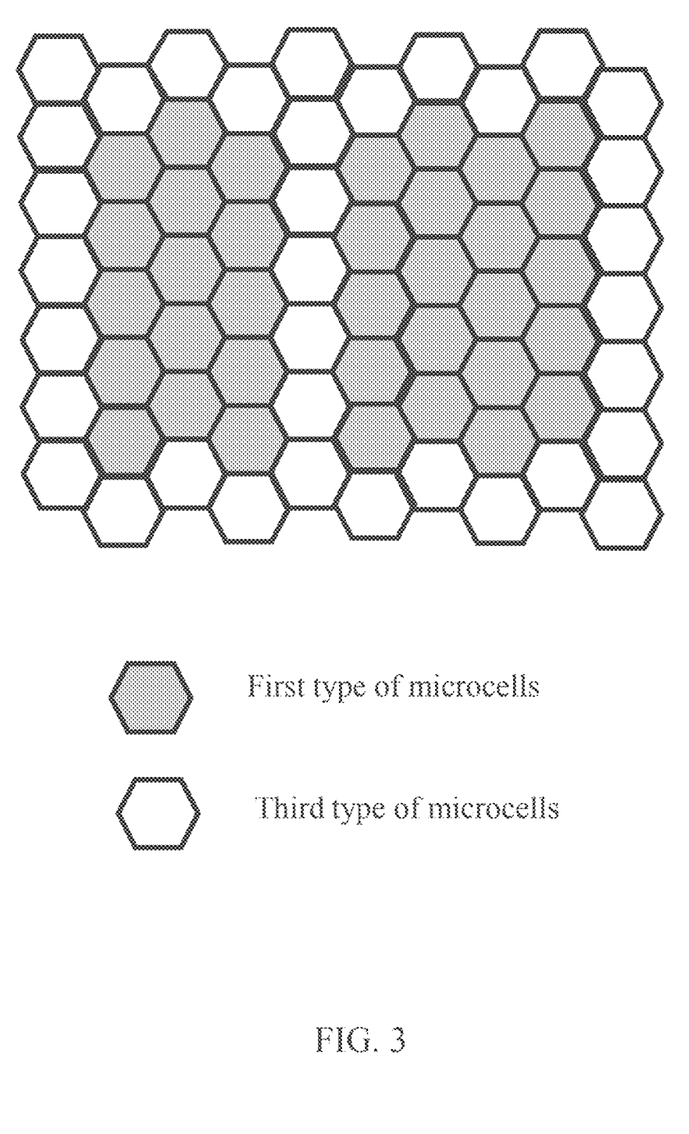
FIG. 3 illustrates an example of an active molecule delivery system having a plurality of a first and a third types of microcells viewed from the top.

A variety of combinations of active molecules is possible, and varying microcells might include hydrophilic pharmaceuticals, hydrophilic nutraceuticals, hydrophilic adjuvants, hydrophilic vitamins, or vaccines. Furthermore, the arrangement of the microcells may not be distributed. Rather the microcells may be filled in clusters, which makes filling and sealing more straightforward. In other embodiments, smaller microcell arrays may be filled with the same medium, i.e., having the same active molecule at the same concentration, and then the smaller arrays assembled into a larger array to make a delivery system of the invention. In other embodiments, differing porosity can be used with differing contents for a microcell. For example, one microcell may include a solution of enzymes and require a porous diffusion layer that has pores large enough for the enzymes to pass, while an adjacent microcell may include a substrate to activate the enzyme, but require a porous diffusion layer with much smaller pores to regulate delivery of the substrate In another embodiment, the active molecule delivery system comprises a first type of microcells and a third type of microcells. The first type of microcells are filled with a first aqueous formulation comprising a first hydrophilic active molecule. The third type of microcells are filled with a third aqueous formulation that does not contain any active molecule. The active molecule delivery system may contain two, three, or more segments of the first type of microcells and two, three, or more segments of the third type of microcells. At least one of the segments of the first type of microcells is surrounded by microcells of the third type of microcells. An example of such a system is illustrated in FIG. 3, which shows an active molecule delivery system having two segments of the first type of microcells, both of which are surrounded by microcells of the third type of microcells. FIG. 3 shows a system having one segment of the third types of microcells. This active molecule delivery system is useful for providing a controlled dose of an active molecule for transdermal delivery. For example, if an active molecule that is present in the first type of microcells is an irritant, the separation of the first type of microcells with microcells of the third type microcells that do not contain an active molecule mitigates the irritation.

The active molecule delivery system of this embodiment, wherein the third type of microcell comprises a formulation having no active molecule, may comprise, in addition to the first and third types of microcells, a second type of microcells filled with a second aqueous formulation comprising a second hydrophilic active molecule. The active molecule delivery system may contain two, three, or more segments of the second type of microcells and one, two, three, or more segments of the third type of microcells. At least one of the segments of the first type of microcells is surrounded by microcells of the third type of microcells. Each of the first type of microcells does not have any adjacent second type of microcells in the layer of microcells of the active molecule delivery system.

In this embodiment, the first, second and third types of microcell comprise an opening and a hydrophobic sealing layer spanning the opening. The first, second and third types of microcell may also comprises a first, second and third porous diffusion layer, respectively, adjacent to the sealing layer. The first, second and third types of microcell may also comprises an adhesive layer adjacent to the sealing layer or adjacent to the first, second, and third porous diffusion layer. The sealing layer may be formed inside each microcell or it may be formed outside the microcell adjacent to each microcell opening. In both cases, the sealing layer may be designed to be different for each microcell type. The same is true for the porous diffusion layer. In other words, the porosity of the sealing layer and/or porous diffusion layer may be different for each type of microcell. This provides an additional control of the amount of each active molecule that is delivered from the system. One way to control the porosity is by the average porous size. Another way to control the porosity is by the thickness of each of the layers (sealing layer, porous diffusion layer, and adhesive layer). It is also possible to use different materials for the construction of these layers of the different types of microcells in the same system.

The active molecule delivery system of the present invention enables the delivery of a combination of active molecules that are not compatible with each other. For example, if the first active molecule is not compatible with the second active molecule and one of both of them degrade in the presence of the other and a first type of microcell is adjacent to a second type of microcell, the two active molecules may contact each other after they exit the microcell, as they diffuse through the porous adhesive layer and/or the porous diffusion layer, and before they are delivered outside the active molecule delivery system. Appropriate separation of the first type of microcell from the second type of microcell by one or more third type of microcells mitigates the potential degradation problem.

Each of the microcells includes walls and an opening. The microcells may be square, round, or polygonal, such as a honeycomb structure. For each first and second types of microcell, the opening is spanned the hydrophobic sealing layer. The hydrophobic sealing layer may be constructed from a variety of materials, such as polyisobutylene, a polyethylene, a polyurethane, a polycaprolactone, or a polysiloxane.

The first and second formulations are aqueous. The first and second aqueous formulations may comprise hydrophilic active molecules. They may also comprise an aqueous carrier that comprises water. They may further comprise water-miscible co-solvent and/or a surfactant. Non-limiting examples of water miscible solvents are dipropylene glycol, tripropylene glycol, diethylene glycol, ethylene glycol, propylene glycol, glycerin, 1,3-propane diol, 2,2-propanediol, 1,2-butanediol, 1,3-butanediol, 1,4-butanediol, 2,3-butanediol, 2-methyl-2,4-pentanediol, and mixtures thereof.

Figure 4:
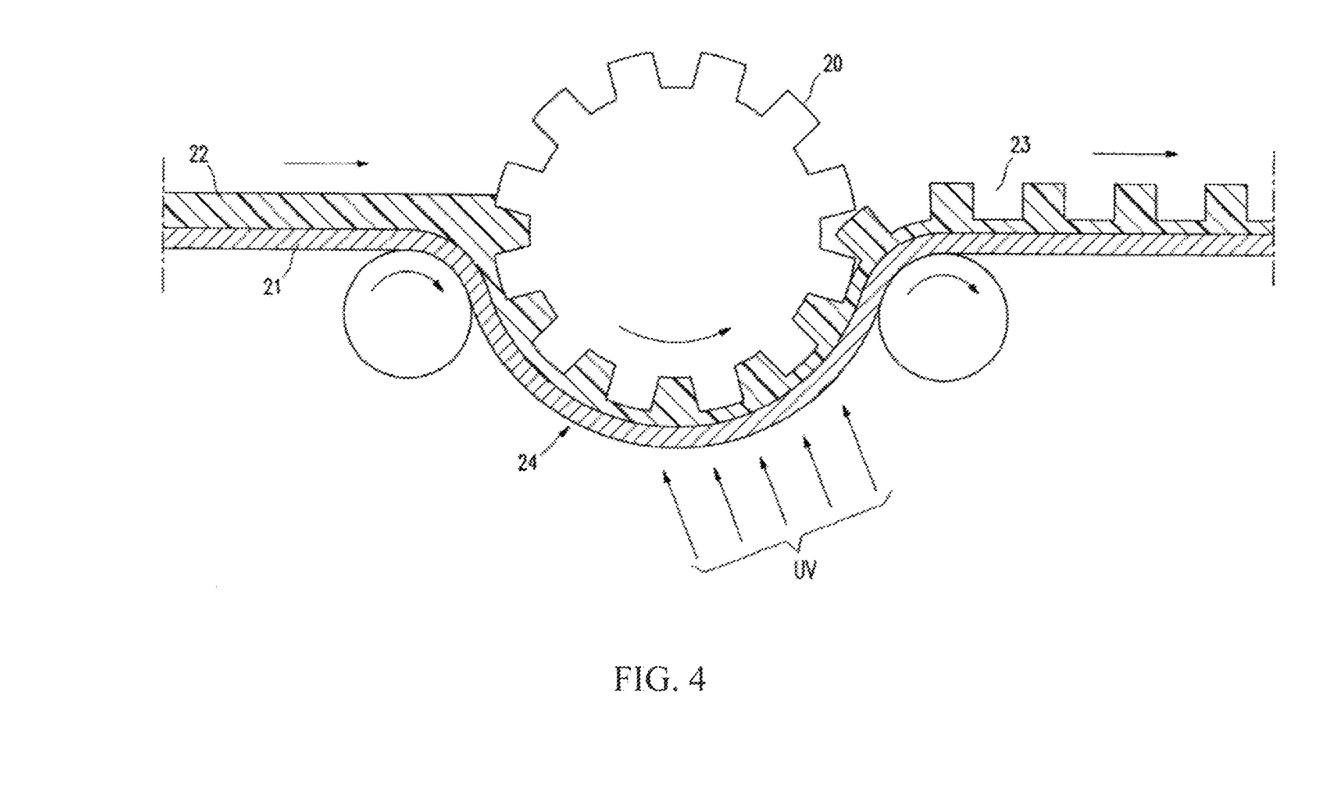
FIG. 4 shows a method for making microcells for the invention using a roll-to-roll process.

Techniques for constructing microcells. Microcells may be formed either in a batchwise process or in a continuous roll-to-roll process as disclosed in U.S. Pat. No. 6,933,098. The latter offers a continuous, low cost, high throughput manufacturing technology for production of compartments for use in a variety of applications including active molecule delivery and electrophoretic displays. Microcell arrays suitable for use with the invention can be created with microembossing, as illustrated in FIG. 4. A male mold 20 may be placed either above the web 24, as shown in FIG. 4, or below the web 24 (not shown); however, alternative arrangements are possible. See U.S. Pat. No. 7,715,088, which is incorporated herein by reference in its entirety. A conductive substrate may be constructed by forming a conductor film 21 on polymer substrate that becomes the backing for a device. A composition comprising a thermoplastic, thermoset, or a precursor thereof 22 is then coated on the conductor film. The thermoplastic or thermoset precursor layer is embossed at a temperature higher than the glass transition temperature of the thermoplastics or thermoset precursor layer by the male mold in the form of a roller, plate or belt.

The thermoplastic or thermoset precursor for the preparation of the microcells may be multifunctional acrylate or methacrylate, vinyl ether, epoxide and oligomers or polymers thereof, and the like. A combination of multifunctional epoxide and multifunctional acrylate is also very useful to achieve desirable physico-mechanical properties. A cross-linkable oligomer imparting flexibility, such as urethane acrylate or polyester acrylate, may be added to improve the flexure resistance of the embossed microcells. The composition may contain polymer, oligomer, monomer and additives or only oligomer, monomer and additives. The glass transition temperatures (or $T_g$) for this class of materials usually range from about −70° C. to about 150° C., preferably from about −20° C. to about 50° C. The microembossing process is typically carried out at a temperature higher than the $T_g$. A heated male mold or a heated housing substrate against which the mold presses may be used to control the microembossing temperature and pressure.

As shown in FIG. 4, the mold is released during or after the precursor layer is hardened to reveal an array of microcells 23. The hardening of the precursor layer may be accomplished by cooling, solvent evaporation, cross-linking by radiation, heat or moisture. If the curing of the thermoset precursor is accomplished by UV radiation, UV may radiate onto the transparent conductor film from the bottom or the top of the web as shown in the two figures. Alternatively, UV lamps may be placed inside the mold. In this case, the mold must be transparent to allow the UV light to radiate through the pre-patterned male mold on to the thermoset precursor layer. A male mold may be prepared by any appropriate method, such as a diamond turn process or a photoresist process followed by either etching or electroplating. A master template for the male mold may be manufactured by any appropriate method, such as electroplating. With electroplating, a glass base is sputtered with a thin layer (typically 3000 Å) of a seed metal such as chrome inconel. The mold is then coated with a layer of photoresist and exposed to UV. A mask is placed between the UV and the layer of photoresist. The exposed areas of the photoresist become hardened. The unexposed areas are then removed by washing them with an appropriate solvent. The remaining hardened photoresist is dried and sputtered again with a thin layer of seed metal. The master is then ready for electroforming. A typical material used for electroforming is nickel cobalt. Alternatively, the master can be made of nickel by electroforming or electroless nickel deposition. The floor of the mold is typically between about 50 to 400 microns. The master can also be made using other microengineering techniques including e-beam writing, dry etching, chemical etching, laser writing or laser interference as described in "Replication techniques for micro-optics", SPIE Proc. Vol. 3099, pp. 76-82 (1997). Alternatively, the mold can be made by photomachining using plastics, ceramics or metals.

Prior to applying a UV curable resin composition, the mold may be treated with a mold release to aid in the demolding process. The UV curable resin may be degassed prior to dispensing and may optionally contain a solvent. The solvent, if present, readily evaporates. The UV curable resin is dispensed by any appropriate means such as, coating, dipping, pouring or the like, over the male mold. The dispenser may be moving or stationary. A conductor film is overlaid the UV curable resin. Pressure may be applied, if necessary, to ensure proper bonding between the resin and the plastic and to control the thickness of the floor of the microcells. The pressure may be applied using a laminating roller, vacuum molding, press device or any other like means. If the male mold is metallic and opaque, the plastic substrate is typically transparent to the actinic radiation used to cure the resin. Conversely, the male mold can be transparent and the plastic substrate can be opaque to the actinic radiation. To obtain good transfer of the molded features onto the transfer sheet, the conductor film needs to have good adhesion to the UV curable resin that should have a good release property against the mold surface.

Figure 5A:
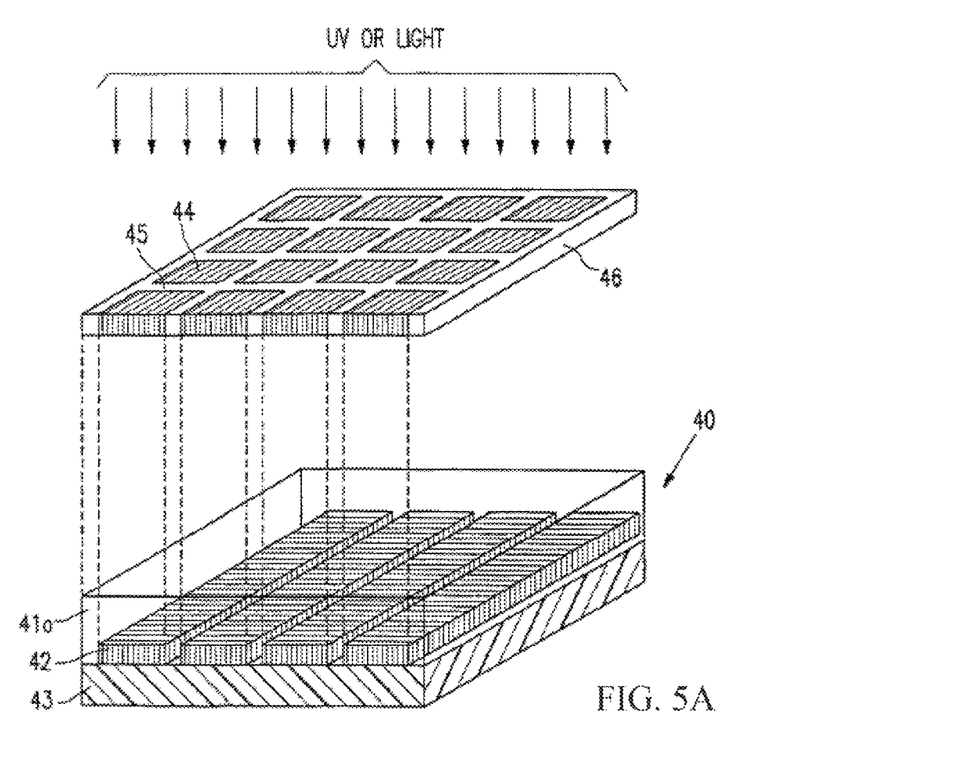
FIGS. 5A and 5B detail the production of microcells for an active molecule delivery system using photolithographic exposure through a photomask of a conductor film coated with a thermoset precursor.
Figure 5B:
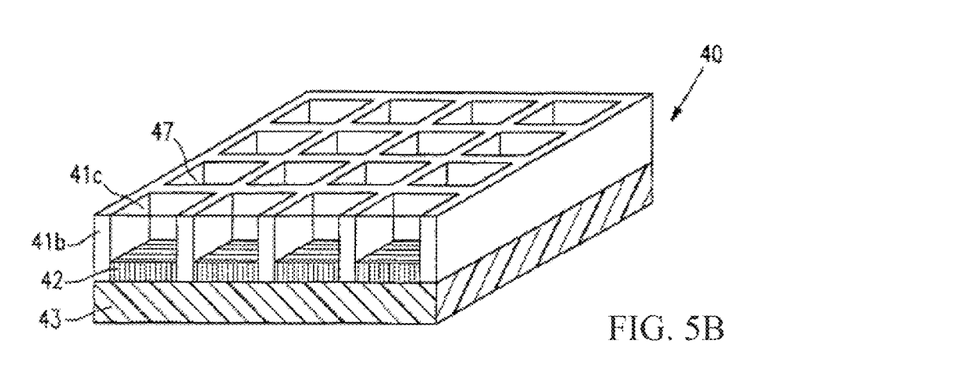

Photolithography. Microcells can also be produced using photolithography. Photolithographic processes for fabricating a microcell array are illustrated in FIGS. 5A and 5B. As shown in FIGS. 5A and 5B, the microcell array 40 may be prepared by exposure of a radiation curable material 41a coated by known methods onto a conductor electrode film 42 to UV light (or alternatively other forms of radiation, electron beams and the like) through a mask 46 to form walls 41b corresponding to the image projected through the mask 46. The base conductor film 42 is preferably mounted on a supportive substrate base web 43, which may comprise a plastic material.

In the photomask 46 in FIG. 5A, the dark squares 44 represent the opaque area and the space between the dark squares represents the transparent area 45 of the mask 46. The UV radiates through the transparent area 45 onto the radiation curable material 41a. The exposure is preferably performed directly onto the radiation curable material 41a, i.e., the UV does not pass through the substrate 43 or base conductor 42 (top exposure). For this reason, neither the substrate 43, nor the conductor 42, needs to be transparent to the UV or other radiation wavelengths employed.

As shown in FIG. 5B, the exposed areas 41b become hardened and the unexposed areas (protected by the opaque area 44 of the mask 46) are then removed by an appropriate solvent or developer to form the microcells 47. The solvent or developer is selected from those commonly used for dissolving or reducing the viscosity of radiation curable materials such as methylethylketone (MEK), toluene, acetone, isopropanol or the like. The preparation of the microcells may be similarly accomplished by placing a photomask underneath the conductor film/substrate support web and in this case the UV light radiates through the photomask from the bottom and the substrate needs to be transparent to radiation.

Figure 5C:
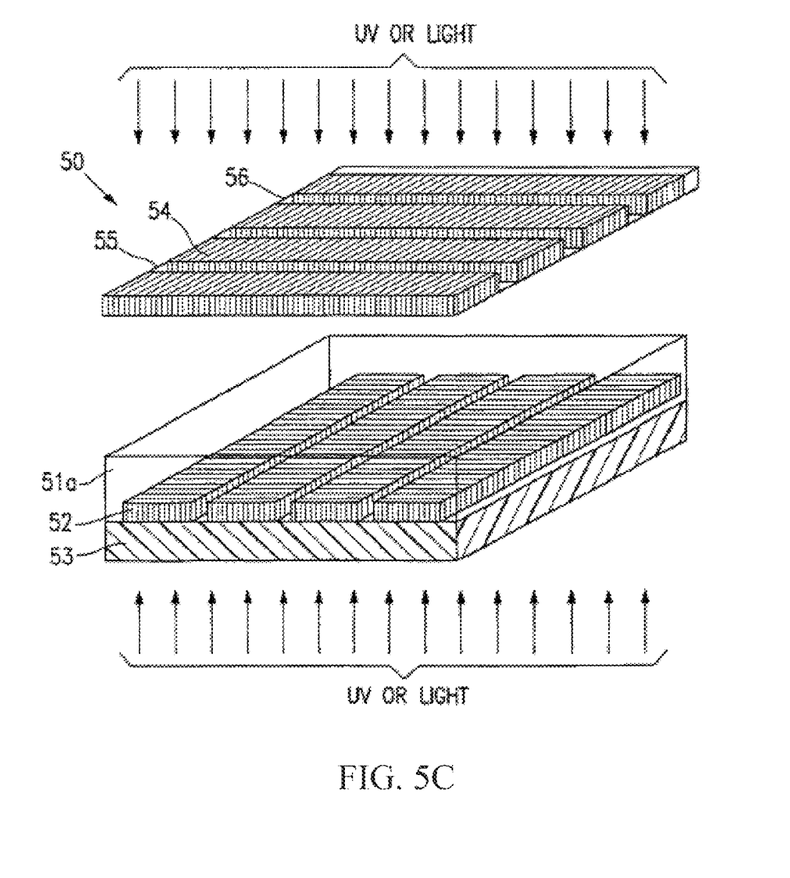
Figure 5D:
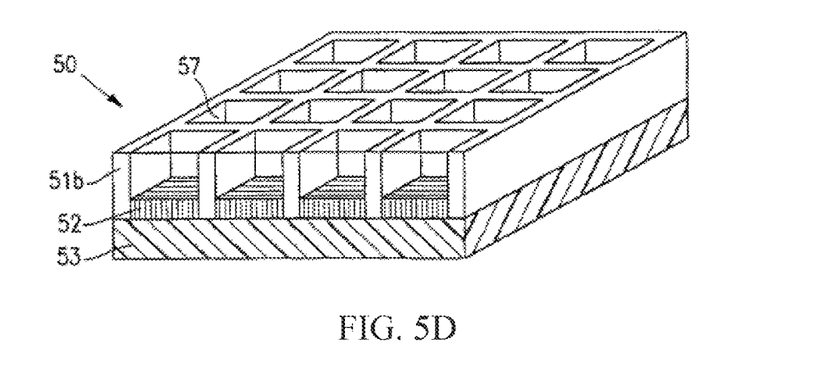

Imagewise Exposure. Still another alternative method for the preparation of the microcell array of the invention by imagewise exposure is illustrated in FIGS. 5C and 5D. When opaque conductor lines are used, the conductor lines can be used as the photomask for the exposure from the bottom. Durable microcell walls are formed by additional exposure from the top through a second photomask having opaque lines perpendicular to the conductor lines. FIG. 5C illustrates the use of both the top and bottom exposure principles to produce the microcell array 50 of the invention. The base conductor film 52 is opaque and line-patterned. The radiation curable material 51a, which is coated on the base conductor 52 and substrate 53, is exposed from the bottom through the conductor line pattern 52, which serves as the first photomask. A second exposure is performed from the "top" side through the second photomask 56 having a line pattern perpendicular to the conductor lines 52. The spaces 55 between the lines 54 are substantially transparent to the UV light. In this process, the wall material 51b is cured from the bottom up in one lateral orientation, and cured from the top down in the perpendicular direction, joining to form an integral microcell 57. As shown in FIG. 5D, the unexposed area is then removed by a solvent or developer as described above to reveal the microcells 57. The technique described in FIGS. 5C and 5D thus allow the different walls to be constructed with different porosity, as needed for the embodiment illustrated in FIG. 2C.

The microcells may be constructed from thermoplastic elastomers, which have good compatibility with the microcells and do not interact with the electrophoretic media. Examples of useful thermoplastic elastomers include ABA, and (AB)n type of di-block, tri-block, and multi-block copolymers wherein A is styrene, α-methylstyrene, ethylene, propylene or norbonene; B is butadiene, isoprene, ethylene, propylene, butylene, dimethylsiloxane or propylene sulfide, and A and B cannot be the same in the formula. The number, n, is ≥1, preferably 1-10 Particularly useful are di-block or tri-block copolymers of styrene or ox-methylstyrene such as SB (poly(styrene-b-butadiene)), SBS (poly (styrene-b-butadiene-b-styrene)), SIS (poly(styrene-b-isoprene-b-styrene)), SEBS (poly(styrene-b-ethylene/butylenes-b-stylene)) poly(styrene-b-dimethylsiloxane-b-styrene), poly((α-methylstyrene-b-isoprene), poly(α-methylstyrene-b-isoprene-b-α-methylstyrene), poly(α-methylstyrene-b-propylene sulfide-b-α-methylstyrene), poly(α-methylstyrene-b-dimethylsiloxane-b-α-methylstyrene). Commercially available styrene block copolymers such as Kraton D and G series (from Kraton Polymer, Houston. Tex.) are particularly useful. Crystalline rubbers such as poly(ethylene-co-propylene-co-5-methylene-2-norbornene) or EPDM (ethylene-propylene-diene terpolymer) rubbers such as Vistalon 6505 (from Exxon Mobil, Houston, Tex.) and their grafted copolymers have also been found very useful.

The thermoplastic elastomers may be dissolved in a solvent or solvent mixture that is immiscible with the display fluid in the microcells and exhibits a specific gravity less than that of the display fluid. Low surface tension solvents are preferred for the overcoating composition because of their better wetting properties over the microcell walls and the electrophoretic fluid. Solvents or solvent mixtures having a surface tension lower than 35 dyne/cm are preferred. A surface tension of lower than 30 dyne/cm is more preferred. Suitable solvents include alkanes (preferably $C_{6-12}$ alkanes such as heptane, octane or Isopar solvents from Exxon Chemical Company, nonane, decane and their isomers), cycloalkanes (preferably $C_{6-12}$ cycloalkanes such as cyclohexane and decalin and the like), alkylbezenes (preferably mono- or di-$C_{1-6}$ alkyl benzenes such as toluene, xylene and the like), alkyl esters (preferably $C_{2-5}$ alkyl esters such as ethyl acetate, isobutyl acetate and the like) and $C_{3-5}$ alkyl alcohols (such as isopropanol and the like and their isomers) Mixtures of alkylbenzene and alkane are particularly useful.

In addition to polymer additives, the polymer mixtures may also include wetting agents (surfactants). Wetting agents (such as the FC surfactants from 3M Company, Zonyl fluorosurfactants from DuPont, fluoroacrylates, fluoromethacrylates, fluoro-substituted long chain alcohols, perfluoro-substituted long chain carboxylic acids and their derivatives, and Silwet silicone surfactants from OSi. Greenwich, Conn.) may also be included in the composition to improve the adhesion of the sealant to the microcells and provide a more flexible coating process. Other ingredients including cross-linking agents (e.g., bisazides such as 4,4'-diazdodiphenyl-methane and 2,6-di-(4'-azidobenzal)-4-methylcyclohexanone), vulcanizers (e.g., 2-benzothiazolyl disulfide and tetramethylthiuram disulfide), multifunctional monomers or oligomers (e.g., hexanediol, diacrylates, trimethylolpropane, triacrylate, divinylbenzene, diallylphthalene), thermal initiators (e.g., dilauroryl peroxide, benzoyl peroxide) and photoinitiators (e.g., isopropyl thioxanthone (ITX). Irgacure 651 and Irgacure 369 from Ciba-Geigy) are also highly useful to enhance the physico-mechanical properties of the sealing layer by crosslinking or polymerization reactions during or after the overcoating process.

After the microcells are produced, they are filled with appropriate mixtures of active molecules. The microcell array 60 may be prepared by any of the methods described above. As shown in cross-section in FIGS. 6A-6D, the microcell walls 61 extend upward from the substrate 63 to form the open cells. The microcells may include a primer layer 62 to passivate the mixture and keep the microcell material from interacting with the mixture containing the active molecule 65. Prior to filling, the microcell array 60 may be cleaned and sterilized to assure that the active molecules are not compromised prior to use.

Figure 6A:
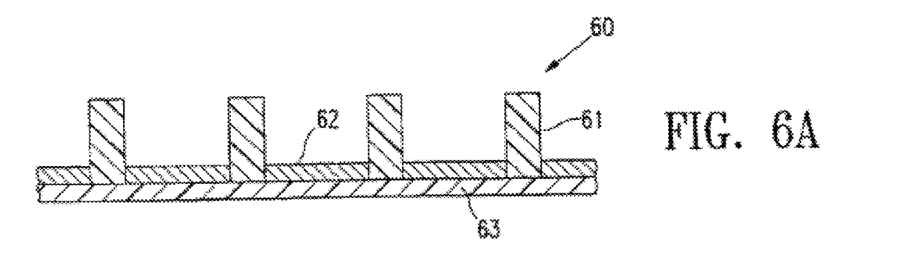
FIGS. 6A-6D illustrate the steps of filling and sealing an array of microcells to be used in an active molecule delivery system.
Figure 6B:
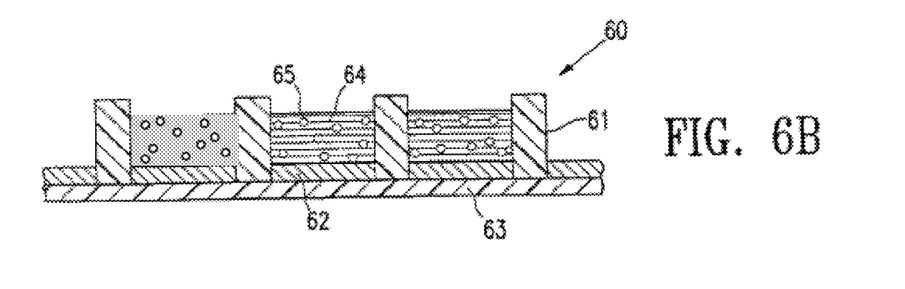

The microcells are next filled with a mixture 64 including active molecules 65. As shown in FIG. 6B, different microcells may include different active molecules. The microcells 60 are preferably partially filled to prevent overflow and the unintentional mixing of active molecules. In systems for delivering hydrophobic active molecules, the mixture may be based upon a biocompatible oil or some other biocompatible hydrophobic carrier. For example, the mixture may comprise a vegetable, fruit, or nut oil. In other embodiments, silicone oils may be used. In systems for delivering hydrophilic active molecules, the mixture may be based upon water or another aqueous medium such as phosphate buffer. The mixture need not be a liquid, however, as hydrogels and other matrices may be suitable to deliver the active molecules 65.

The microcells may be filled using a variety of techniques. In some embodiments, where a large number of neighboring microcells are to be filled with an identical mixture, blade coating may be used to fill the microcells to the depth of the microcell walls 61. In other embodiments, where different mixtures are to be filled in a variety of nearby microcell, inkjet-type microinjection can be used to fill the microcells. In yet other embodiments, microneedle arrays may be used to fill an array of microcells with the correct mixtures. The filling may be done in a one-step, or a multistep process. For example, all of the cells may be partially filled with an amount of solvent. The partially filled microcells are then filled with a second mixture including the one or more active molecules to be delivered.

Figure 6C:
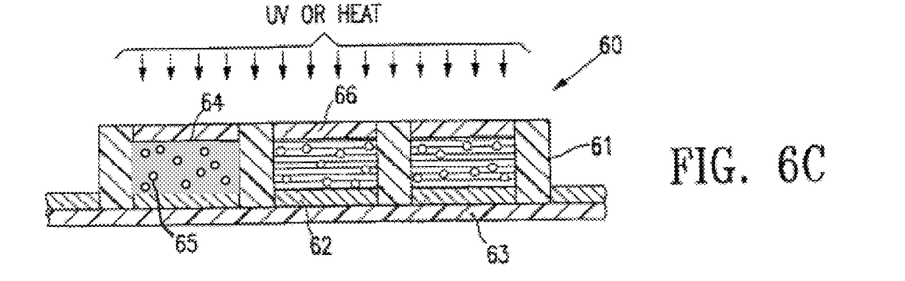

As shown in FIG. 6C, after filling, the microcells are sealed by applying a polymer 66 that becomes the porous diffusion layer. In some embodiments, the sealing process may involve exposure to heat, dry hot air, or UV radiation. In most embodiments, the polymer 66 will be compatible with the mixture 64, but not dissolved by the solvent of the mixture 64. The polymer 66 will also be biocompatible and selected to adhere to the sides or tops of the microcell walls 61. A suitable biocompatible adhesive for the porous diffusion layer is a phenethylamine mixture, such as described in U.S. patent application Ser. No. 15/336,841, filed Oct. 30, 2016 and titled "Method for Sealing Microcell Containers with Phenethylamine Mixtures," which is incorporated herein by reference in its entirety. Accordingly, the final microcell structure is mostly impervious to leaks and able to withstand flexing without delamination of the porous diffusion layer.

In alternate embodiments, a variety of individual microcells may be filled with the desired mixture by using iterative photolithography. The process typically includes coating an array of empty microcells with a layer of positively working photoresist, selectively opening a certain number of the microcells by imagewise exposing the positive photoresist, followed by developing the photoresist, filling the opened microcells with the desired mixture, and sealing the filled microcells by a sealing process. These steps may be repeated to create sealed microcells filled with other mixtures. This procedure allows for the formation of large sheets of microcells having the desired ratio of mixtures or concentrations.

Figure 6D:
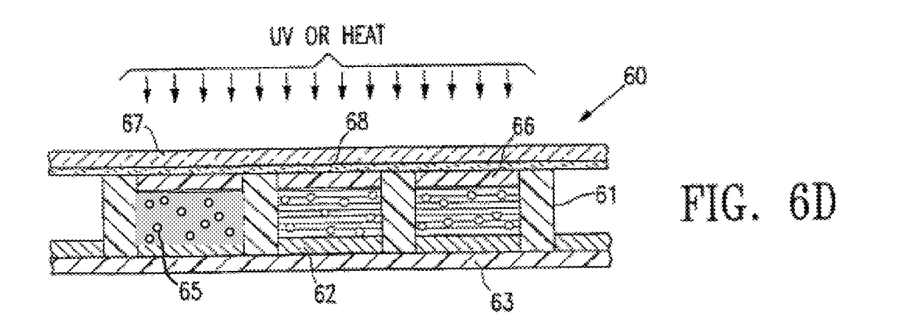

After the microcells 60 are filled, the sealed array may be laminated with a finishing layer 68 that is also porous to the active molecules, preferably by pre-coating the finishing layer 68 with an adhesive layer, which may be a pressure sensitive adhesive, a hot melt adhesive, or a heat, moisture, or radiation curable adhesive. The laminate adhesive may be post-cured by radiation such as UV through the top conductor film if the latter is transparent to the radiation. In some embodiments, a biocompatible adhesive 67 is then laminated to the assembly. The biocompatible adhesive 67 will allow active molecules to pass through while keeping the device mobile on a user. Suitable biocompatible adhesives are available from 3M (Minneapolis, Minn.).

Once the delivery system has been constructed, it may be covered with an encapsulating covering to provide protection against physical shock. The encapsulating covering may also include adhesives to make sure that the active molecule delivery system stays affixed, e.g., to a patient's back. The encapsulating covering may also include aesthetic coloring or fun designs for children.

Example—Microcell Assembly Filled with Aqueous Solution

Figure 7:
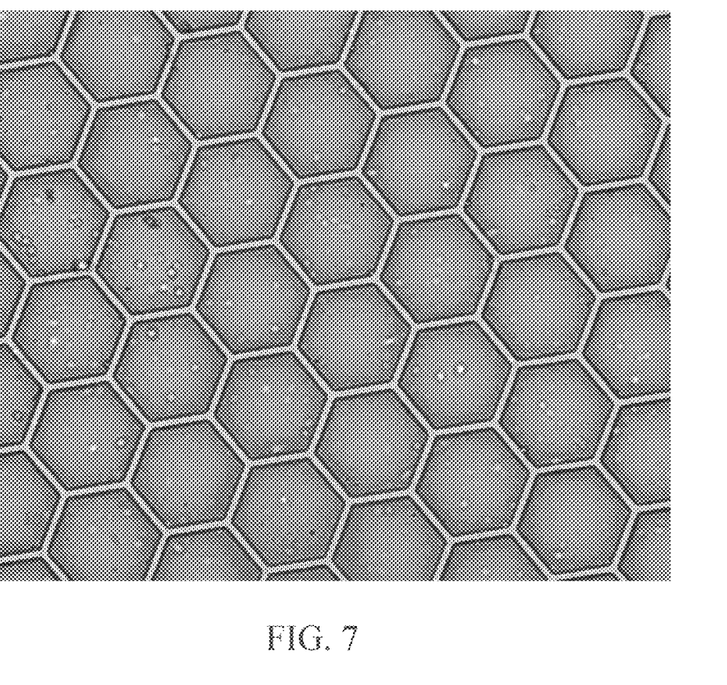
FIG. 7 is a microscopic image of a layer of microcells filled with an aqueous formulation that is dyed with blue food coloring. The cells are sealed with a hydrophobic sealing layer comprising polyisobutylene.

A hydrophilic molecule delivery system including microcells, a hydrophobic sealing layer, and a porous diffusion layer was constructed. A microcell layer was prepared by microembossing polyethylene terephthalate (PET) as described above. Next, an aqueous solution was prepared comprising 5.0 weight percent of nicotine, and 5 weight percent of ethylene vinyl alcohol copolymer (RS1717 from Kuraray) in deionized water by weight of the aqueous solution. To improve visualization, blue food coloring was added to the solution. The microcells were filled with the colored solution using a pipette, and the remnant solution was removed with a rubber spatula. The filled microcells were overcoated with a 10 weight percent solution of polyisobutylene (PIB) in xylene by weight of the solution. The PIB in the sealing layer had an average molecular weight of 850,000 Daltons. A wet coating thickness of 8 mils (0.21032 mm) of the solution was applied and subsequently dried to create a hydrophobic sealing layer. A microscope view of the filled and sealed microcell layer is shown in FIG. 7.

Figure 8:
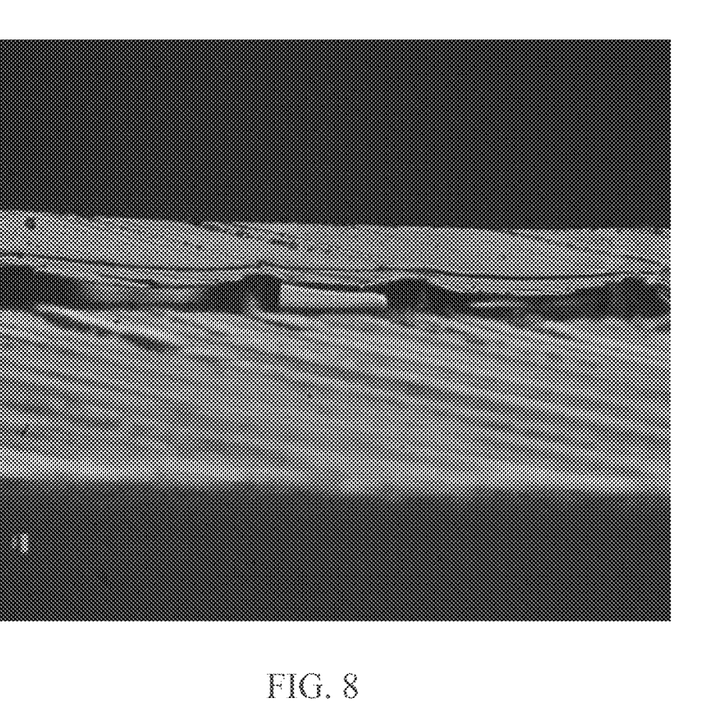
FIG. 8 shows a microscope image of polyisobutylene sealing layer and the porous diffusion layer formed from an acrylic/methacrylic acid copolymer (EUDRAGIT®, Evonik, Essen, Del.).

After the sealing layer was cured, a porous diffusion layer was formed on top of the sealing layer. The porous diffusion layer was made from a 30 weight percent of Eudragit E100 (in MEK) by weight of the solution. Eudragit E100 is a commercial copolymer comprising dimethylaminoethyl methacrylate, butyl methacrylate, and methyl methacrylate, available from Evonic GmbH (Essen, Germany). A wet coating thickness of 10 mils (0.254 mm) of the solution was applied and dried to create the porous diffusion layer. As shown in FIG. 8, the Eudragit, together with PIB, produces a uniform barrier with a well-defined aqueous volume inside the microcell. While not shown here, an adhesive layer may be applied directly to the porous diffusion layer to facilitate long-term placement of the active molecule delivery system.

Example 2

The procedure of Example 1 was repeated with the following difference. The porous diffusion layer was formed from a 20 weight percent of Eudragit E100 (in MEK) by weight of the solution. A wet coating thickness of 8 mils of the solution was applied and dried to create the porous diffusion layer. The porous diffusion layer of the active molecule delivery system of Example 1 has larger thickness than the porous diffusion layer of the active molecule delivery system of Example 2. In addition, the pore size of the active molecule delivery system of Example 1 has average pore size that is smaller than the average pore size of the porous diffusion layer of the active molecule delivery system of Example 2.

Example 3

The procedure of Example 1 was repeated with the following difference. The hydrophobic sealing layer was formed using a 5 weight percent of solution of polyisobutylene (PIB) in xylene by weight of the solution. The PIB in the sealing layer of Example 3 had an average molecular weight of 4,200,000 Daltons. A wet coating thickness of 8 mil of the solution was applied and dried to create the hydrophobic sealing layer. The sealing layer of the active molecule delivery system of Example 1 has a longer release pathway than the sealing layer of the active molecule delivery system of Example 3.

Example 4

Figure 9:
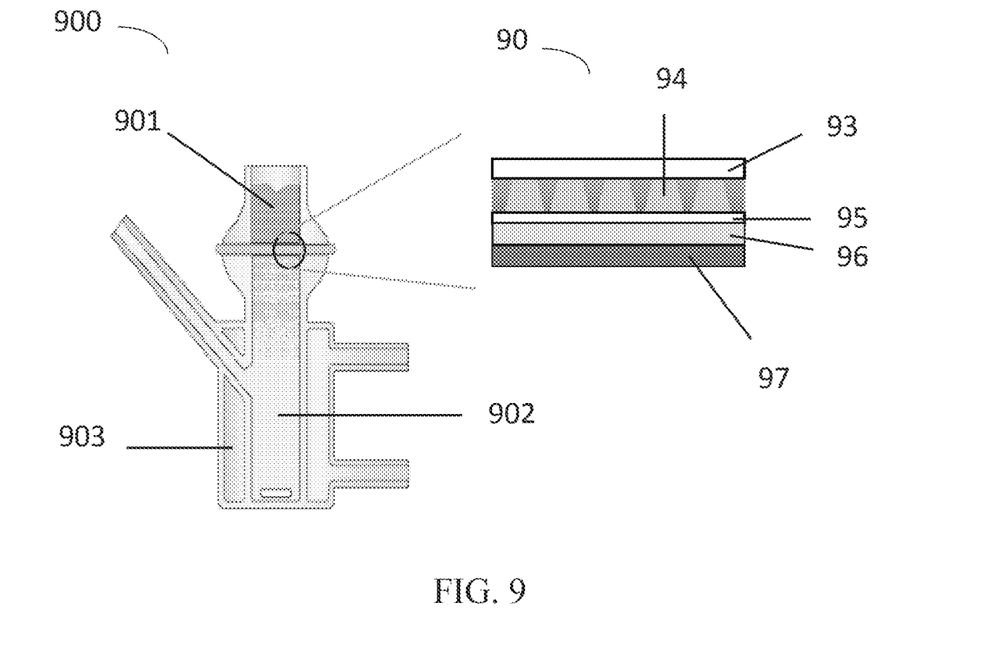
FIG. 9 illustrates an experimental set up for the determination of the transdermal delivery profile of the active molecule delivery system of the present invention using a Frenz cell.
Figure 10:
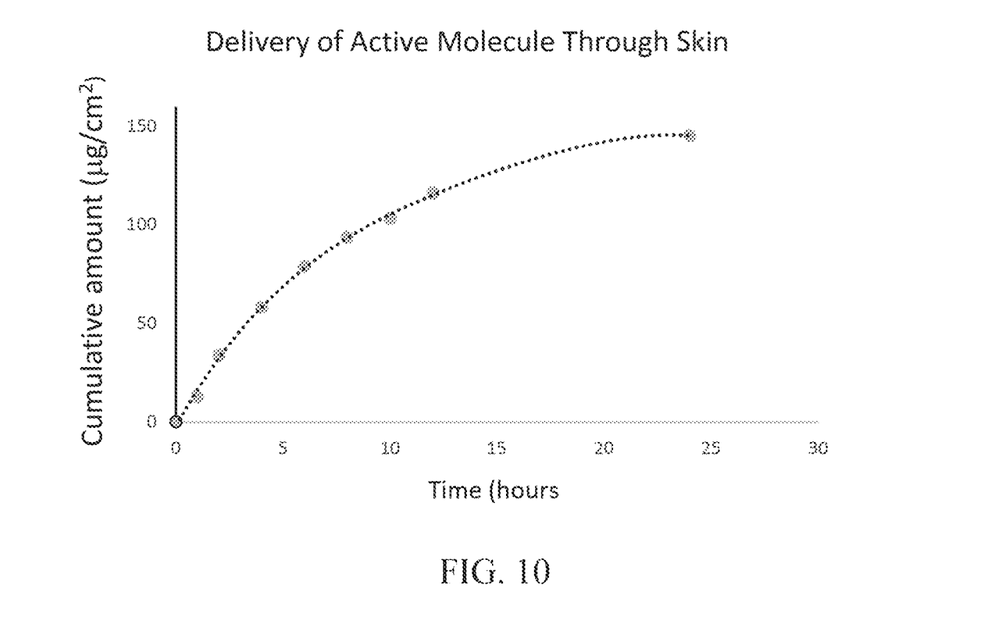
FIG. 10 shows the active molecule delivery profile of an actual example of the active molecule delivery system of the present invention.

A nude mouse skin sample was placed on the porous diffusion layer of the active molecule delivery system of Example 2. Then, the active molecule delivery system was placed in contact with the top opening of the receptor compartment of a Franz cell. That is, the nude mouse skin sample was placed between the porous diffusion layer of the active molecule delivery system of Example 2 and the top opening of the receptor of the Franz cell. This experimental set up is shown in FIG. 9. The active molecule delivery system of Example 2(90) comprises a backing barrier 93, microcells 94 comprising the aqueous active molecule formulation of Example 1, sealing layer 95, porous diffusion layer 96, and the nude mouse skin sample 97. The Franz cell 900 comprises an empty donor chamber 901, and a receptor chamber 902 fitted with a condenser 903. The receptor chamber 902 contained phosphate-buffered saline (PBS): ethanol at 60:40 ratio. Active molecule from the microcells 94 of the active molecule delivery system 90 diffused through the sealing layer 95, the porous diffusion layer 96 and the nude mouse skin sample 97 into the receptor chamber 902. A sample of the receptor solution was withdrawn after 1, 2, 4, 6, 8, 10, 12 and 24 hours and the amount of nicotine was determined analytically. The graph of FIG. 10 provides the results of the cumulative amount of nicotine that reached the receptor chamber 902 in sg/cm². As shown in FIG. 10, there is control transdermal delivery of the active molecule from the active molecule delivery system of the present invention.

Thus, the invention provides for a hydrophilic active molecule delivery system including a plurality of microcells. The microcells may include differing hydrophilic active molecules, or differing concentrations of hydrophilic active molecules. This disclosure is not limiting, and other modifications to the invention, not described, but self-evident to one of skill in the art, are to be included in the scope of the invention.

The invention claimed is:

1. An active molecule delivery system including a layer of microcells, the layer of microcells comprising:

a plurality of a first type of microcells filled with a first aqueous formulation comprising a first hydrophilic active molecule;

a plurality of a second type of microcells filled with a second aqueous formulation comprising a second hydrophilic active molecule, wherein the first and second active molecules are different;

a plurality of a third type of microcells that do not contain any aqueous formulation comprising an active molecule;

wherein each microcell of the pluralities of the first, second, and third types of microcells includes walls and an opening;

wherein each microcell of the pluralities of the first and second types of microcells includes a hydrophobic sealing layer spanning the opening;

wherein at least one microcell of the first type of microcells does not have any adjacent microcell of the second type of microcells in the layer of microcells; and wherein the plurality of the third type of microcells does not include a sealing layer spanning the opening.

2. The active molecule delivery system of claim 1, wherein each of the first type microcells does not have any adjacent second type of microcells in the layer of microcells.

3. The active molecule delivery system of claim 1, wherein each of the plurality of the first and second types of microcells further comprises an adhesive layer adjacent to the hydrophobic sealing layer.

4. The active molecule delivery system of claim 1, wherein at least one of the first type of microcells is separated from the second type of microcells by three or more of the third type of microcells.

5. The active molecule delivery system of claim 3, wherein the plurality of the first type of microcells further comprises a first porous diffusion layer between the hydrophobic sealing layer and the adhesive layer, and the plurality of the second type of microcells further comprises a second porous diffusion layer between the hydrophobic sealing layer and the adhesive layer.

6. The active molecule delivery system of claim 5, wherein the porous diffusion layer comprises an acrylate, a methacrylate, a polycarbonate, a polyvinyl alcohol, cellulose, poly(N-isopropylacrylamide) (PNIPAAm), poly(lactic-co-glycolic acid) (PLGA), polyvinylidene chloride, acrylonitrile, amorphous nylon, oriented polyester, terephthalate, polyvinyl chloride, polyethylene, polypropylene, polybutylene, polyisobutylene, or polystyrene.

7. The active molecule delivery system of claim 5, wherein the porous diffusion layer has an average pore size of between 10 nm and 100 µm.

8. The active molecule delivery system of claim 1, wherein the first hydrophilic active molecule is a pharmaceutical compound or an aroma compound.

9. The active molecule delivery system of claim 1, wherein the first hydrophilic active molecule comprises nucleic acids or amino acids.

10. The active molecule delivery system of claim 1, wherein each of the plurality of the first, second, and third microcells has a volume greater than 100 nL.

11. The active molecule delivery system of claim 1, further comprising an encapsulating cover that encapsulates the active molecule delivery system.

12. The active molecule delivery system of claim 3, further comprising a backing layer in contact with the adhesive layer.

13. The active molecule delivery system of claim 1, wherein the first aqueous formulation additionally includes a thickening agent.

14. The active molecule delivery system of claim 5, wherein the first porous diffusion layer has average pore size that is larger than the average pore size of the second porous diffusion layer.

15. The active molecule delivery system of claim 1, wherein the first hydrophilic active molecule is an enzyme, and wherein the second active molecule is a substrate that can activate the enzyme.

16. An active molecule delivery system including a layer of microcells, the layer of microcells comprising:
   a plurality of a first type of microcells filled with a first aqueous formulation comprising a first hydrophilic active molecule;
   a plurality of a third type of microcells filled with a third aqueous formulation that does not comprise any active molecules;
   wherein each microcell of the first and third types includes walls and an opening;
   wherein each microcell of the first and third types includes a hydrophobic sealing layer spanning the opening;
   wherein the active molecule delivery system comprises one or more segments of the first type of microcells, wherein each segment of the first type of microcells exclusively comprises only microcells of the first type of microcells, and wherein all the microcells of the first type of microcells that are adjacent to any other microcell of the segment of the first type of microcells are members of the same segment; and
   wherein the periphery of at least one segment of the first type of microcells is surrounded by microcells of the third type of microcells.

17. The active molecule delivery system of claim 16, further comprising a plurality of a second type of microcells filled with a second aqueous formulation comprising a second hydrophilic active molecule,
   wherein each microcell of the second type includes walls and an opening;
   wherein each microcell of the second type includes a hydrophobic sealing layer spanning the opening;
   wherein the active molecule delivery system comprises one or more segments of the second type of microcells, wherein each segment of the second type of microcells exclusively comprises only microcells of the second type of microcells, and all the microcells of the second type of microcells that are adjacent to any other microcell of the segment of the second type of microcells are members of the same segment;
   wherein the periphery of at least one segment of the second type of microcells is surrounded by microcells of the third type of microcells; and
   wherein each of the first type microcells does not have any adjacent second type of microcells in the layer of microcells.

18. The active molecule delivery system of claim 17, wherein each of the plurality of the first, second, and third types of microcells further comprises a porous diffusion layer adjacent to the hydrophilic sealing layer.

19. The active molecule delivery system of claim 18, wherein each of the plurality of the first, second, and third types of microcells further comprises an adhesive layer, wherein the porous diffusion layer is disposed between the sealing layer and the adhesive layer.

* * * * *